United States Patent [19]

Kametani et al.

[11] 4,301,297

[45] Nov. 17, 1981

[54] PROCESS FOR PREPARING DIMETHYLAMINOETHYL METHACRYLATE

[75] Inventors: Yoshiya Kametani; Yasuo Iino, both of Yokohama, Japan

[73] Assignee: Nitto Chemical Industry Co., Ltd., Tokyo, Japan

[21] Appl. No.: 848,523

[22] Filed: Nov. 4, 1977

[30] Foreign Application Priority Data

Nov. 26, 1976 [JP] Japan ................................ 51-141306

[51] Int. Cl.$^3$ ............................................. C07C 67/03
[52] U.S. Cl. ................................................... 560/217
[58] Field of Search .................. 560/217, 222, 99, 234

[56] References Cited

U.S. PATENT DOCUMENTS

| | | | |
|---|---|---|---|
| 2,720,507 | 10/1955 | Caldwell | 560/99 |
| 3,341,570 | 9/1967 | Barie, Jr. | 560/99 |
| 3,642,877 | 2/1972 | Jayawant | 560/217 |
| 3,714,234 | 1/1973 | White | 560/217 |

FOREIGN PATENT DOCUMENTS 810381  6/1955  United Kingdom .

Primary Examiner—Natalie Trousof
Assistant Examiner—L. Hendriksen
Attorney, Agent, or Firm—Cushman, Darby & Cushman

[57] ABSTRACT

Dimethylaminoethyl methacrylate, which is a useful monomer for the production of polymers useful as flocculants, antistatic agents, soil improving agents, etc., having a high purity can be prepared in a high yield by subjecting methyl methacrylate and dimethylaminoethanol to transesterification in the presence of di-n-octyltin oxide as a catalyst.

7 Claims, No Drawings

PROCESS FOR PREPARING DIMETHYLAMINOETHYL METHACRYLATE

The present invention relates to a process for preparing dimethylaminoethyl methacrylate which comprises subjecting methyl methacrylate and dimethylaminoethanol to transesterification.

The process for preparing dimethylaminoethyl methacrylate which comprises subjecting methyl methacrylate and dimethylaminoethanol to transesterification is known and proceeds as represented by the following reaction formula, $CH_2 = CCH_3COOCH_3 + HOCH_2CH_2N(CH_3)_2$

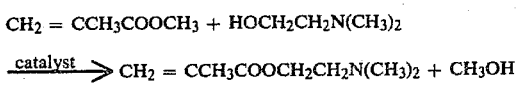

$\xrightarrow{catalyst} CH_2 = CCH_3COOCH_2CH_2N(CH_3)_2 + CH_3OH$

It is generally known to use in the transesterification reaction an alkali metal alkoxide such as sodium methoxide ($NaOCH_3$) as a catalyst.

If the said transesterification reaction is performed in the presence of an alkali metal alkoxide as a catalyst, however, the activity of the catalyst is reduced during the reaction and thereby the catalyst must be replenished many times during the reaction. It is very troublesome.

Also, these catalysts have defects in that they cause during the reaction a side reaction of adding dimethylaminoethanol as a starting material or methanol formed as a by-product to the double bond in methyl methacrylate as a starting material and that they cause also, when the reaction mixture is distilled after the reaction to recover the desired product, a side reaction of adding the unreacted alcohol or the alcohol formed as a by-product to the double bond in the dimethylaminoethyl methacrylate as a desired product.

Alternatively, the use of a titanium alkoxide as a catalyst is proposed. This catalyst is expensive and its activity is lost by the presence of a very small amount of moisture in the reaction system. Therefore, the moisture in the reaction system must be previously removed completely when these catalysts are used.

Further, the use of di-n-butyltin oxide as a catalyst is proposed in U.S. Pat. No. 3,642,877.

Although this catalyst has an advantage in that side reactions can be suppressed by the use of the catalyst, the catalyst has a defect in that the activity of the catalyst is also lost by the presence of a very small amount of moisture in the reaction system.

It is described in the U.S. patent specification that the moisture in the reaction system must be maximally removed before the catalyst is added to the reaction system since the di-n-butyltin oxide catalyst is inactivated by the moisture. When methyl methacrylate and dimethylaminoethanol are subjected to transesterification in the presence of the catalyst, the starting materials comprising methyl methacrylate, dimethylaminoethanol and a small amount of a polymerization retarder must be heated prior to the addition of the catalyst to remove the moisture in the system as the starting methyl methacrylate azeotrope.

When di-n-butyltin oxide is used as a catalyst, therefore, not only the operations are troublesome but also it is difficult to handle owing to its strong toxicity. Also, it can not be said that the reaction result (the yield of the desired product) obtained by the use of it is good.

An object of the present invention is to provide a process for preparing dimethylaminoethyl methacrylate more advantageously than prior art processes.

Another object of the invention is to provide a process for preparing dimethylaminoethyl methacrylate by transesterification between methyl methacrylate and dimethylaminoethanol in the presence of a catalyst.

Another object of the invention is to provide a catalyst for said transesterification reaction which has not the above-mentioned defects of the prior art catalysts.

The other objects and advantages of the present invention will be apparent from the following description.

As a result of an extensive study, it has now been found that these objects can be attained by the use of di-n-octyltin oxide as a catalyst.

According to the present invention, there is provided a process for preparing dimethylaminoethyl methacrylate which comprises subjecting methyl methacrylate and dimethylaminoethanol to transesterification, characterized by using di-n-octyltin oxide as a catalyst.

In the process of the present invention, side reactions such as addition of dimethylaminoethanol or methanol formed as a by-product to the double bond in methyl methacrylate do substantially not occur in the step of transesterification between methyl methacrylate and dimethylaminoethanol. Further, even in the step of recovering the desired product by distilling the reaction mixture after the reaction, a side reaction of adding the unreacted alcohol or the alcohol formed as a by-product to the double bond in the desired product substantially does not occur. Thereby, it is possible to obtain the desired product having a high purity in a high yield.

Also, the catalyst used in the present invention does not lose its activity during the reaction. Therefore, the catalyst may be added to the reaction system at once when the reaction is started. Thus, the operation is simple.

Further, the catalyst used in the present invention is less affected by the presence of a very small amount of moisture in the reaction system than di-n-butyltin oxide. Therefore, it is unnecessary to remove the moisture in the reaction system completely prior to the reaction.

Commercially available methyl methacrylate contains substantially no moisture, but dimethylaminoethanol usually contains about 0.1 to about 0.5% by weight of moisture. When di-n-butyltin oxide is used as a catalyst, therefore, the moisture must be removed before the catalyst is added. Otherwise the yield of the desired product is remarkably reduced. If di-n-octyltin oxide is used as a catalyst according to the present invention, however, it is unnecessary to remove such an amount of moisture. Even if the moisture is not removed, the yield of the desired product is not reduced. Further, the yield obtained when the moisture is not removed is rather higher than the yield obtained by the use of di-n-butyltin oxide as a catalyst in a completely dehydrated system.

Also, di-n-octyltin oxide is lower than di-n-butyltin oxide in toxicity. For example, an $LD_{50}$ value of di-n-butyltin oxide obtained when it is administered to rats orally in admixture with an edible oil is 520 mg/kg and its $LD_{50}$ value obtained when it is administered to rats orally in admixture with Tylose (an aqueous cellulose ether solution manufactured by Farbwerke Hoechst AG in West Germany) is 800 mg/kg. On the other hand, the $LD_{50}$ value of di-n-octyltin oxide obtained when it is administered to rats orally in admixture with a mixture of an edible oil and Tylose is 2500 mg/kg [O.

R. Klimmer, Arzneim-Forsch., Vol. 19, pages 934–939 (1969)].

Therefore, di-n-octyltin oxide is easier to handle than di-n-butyltin oxide. Further, di-n-octyltin oxide is available at low prices since it is useful as a raw material for the production of a stabilizer for vinyl chloride resin.

The amount of the catalyst used in the practice of the present invention is usually 0.1 to 5% by mole, and preferably 0.25 to 2.5% by mole, based on the dimethylaminoethanol as a starting material. The catalyst used in the present invention is generally soluble in the reactants. Thereby, the development of its catalytic activity is rapid and the reaction velocity of the reaction between methyl methacrylate and dimethylaminoethanol can be increased.

The amount of methyl methacrylate used is usually 1.2 to 3.5 moles, and preferably 1.5 moles or more, per mole of dimethylaminoethanol.

In the reaction, a polymerization inhibitor may be added to the reaction system to prevent the polymerization of methyl methacrylate as a starting material and dimethylaminoethyl methacrylate as a desired product. The polymerization inhibitors generally used include phenothiazine, hydroquinone monomethyl ether, phenyl-$\beta$-naphthylamine, paraphenylenediamine and diphenylamine. Particularly, phenothiazine is a preferable polymerization inhibitor.

The reaction temperature is usually 40° to 140° C., and preferably 60° to 130° C. At temperatures of less than 40° C., the activity of the catalyst is low. Also, the reaction temperature of more than 140° C. is not preferable in that side reactions such as polymerization, etc. become easy to occur at such temperatures.

Although the reaction may be conducted under atmospheric pressure, it is preferable to carry out the reaction under a slightly reduced pressure since the methanol formed as a by-product can be rapidly distilled off from the reaction system.

In the practice of the reaction, it is unnecessary to supply the catalyst in portions but a required amount of the catalyst may be added at a stretch on the start of the reaction.

The reaction solvent is generally not required, but may be used. Examples of the solvent used include benzene, toluene and hexane.

The methanol as formed as a by-product in the reaction shows azeotropy with the unreacted methyl methacrylate. During the reaction, therefore, the azeotropic mixture is led to a distilling column where part of the mixture is withdrawn from the reaction system while the mixture is refluxed into the reaction system at a suitable reflux ratio. The reflux ratio is usually decided to be 5:1 to 50:1.

General embodiment of the present invention will be explained. First of all, appointed amounts of starting materials, a catalyst, a polymerization inhibitor, and optionally a solvent are charged into and heated in a reactor equipped with a thermometer and a distilling column. The mixture is reacted for some time under complete reflux (the temperature of the reaction mixture about 100° C.). At the point where reflux became violent part of the azeotropic mixture of methanol formed as a by-product and methyl methacrylate is withdrawn from the system at a reflux ratio of about 5:1 to 50:1. During the reaction, the temperature at the top of the distilling column is kept at about 55° to 70° C.

With the progress of the reaction, the temperature at the top of the distilling column and the temperature of the reaction mixture increase. In order to prevent side reactions and the formation of polymers, it is desirable to keep the temperature of the reaction mixture at 130° C. or less.

The reaction time varies according to a molar ratio of the starting materials, the reaction temperature, a reflux ratio, etc., but is usually within 5 hours. When the reaction approaches the end, the temperature at the top of the distilling column increases suddenly.

The state of the reaction may be checked by measuring the conversion of dimethylaminoethanol as a starting material in the reaction liquid by gas chromatography.

After the reaction, the reaction mixture is distilled under reduced pressure according to a usual method. The unreacted methyl methacrylate is first distilled off and the desired product, dimethylaminoethyl methacrylate, is then distilled off.

Dimethylaminoethyl methacrylate produced according to the present invention is a compound useful as a raw material for the production of cationic polymers which may be used as an antistatic agent, a soil improving agent, an electroconductive processing agent, a paper treating agent, a flocculant, etc.

The following example illustrates the present invention.

EXAMPLE

Into a flask equipped with a stirrer, a thermometer and a distilling column are charged 750.8 g of methyl methacrylate, 268.7 g of dimethylaminoethanol containing a small amount of moisture, 6.0 g of phenothiazine as a polymerization inhibitor, and 10.6 g of di-n-octyltin oxide as a catalyst. The mixture is heated with stirring until it boils.

The azeotropic mixture of methanol formed as a by-product and methyl methacrylate as a starting material is refluxed for about 20 minutes and the reaction mixture is then reacted while part of the azeotropic mixture is withdrawn from the system at a reflux ratio of 15:1. During the reaction, the temperature at the top of the distilling column is kept at 65°–75° C. The transesterification reaction is completed in 4.5 hours.

After the reaction, the reaction mixture is distilled under reduced pressure to obtain a fraction at 83° to 63.5° C. at 21 to 5 mmHg.

As a result of the analysis of this fraction by infrared spectroscopic analysis and nuclear magnetic resonance, it is confirmed that the fraction is dimethylaminoethyl methacrylate.

The yields of dimethylaminoethyl methacrylate obtained by carrying out the above-mentioned experiment by the use of dimethylaminoethanols containing different amounts of moisture as a starting material are shown in Table 1.

TABLE 1

| Moisture in the starting ethanol (% by weight) | 0.5 | 0.3 | 0.1 |
|---|---|---|---|
| Yield of dimethylamino-* ethyl methacrylate (%) | 93.0 | 95.7 | 96.1 |

*Based on the starting ethanol

For comparison, dimethylaminoethyl methacrylate is prepared in the same manner except that di-n-octyltin oxide is replaced by di-n-butyltin oxide. The results obtained are shown in Table 2.

TABLE 2

| Moisture in the starting ethanol (% by weight) | 0.5 | 0.3 | 0.1 |
|---|---|---|---|
| Yield of dimethylamino-* ethyl methacrylate (%) | 77.4 | 83.7 | 90.8 |

*Based on the starting ethanol

As is seen from comparison between Table 1 and Table 2, when methyl methacrylate and dimethylaminoethanol are subjected to transesterification in a reaction system containing a small amount of moisture, the use of di-n-octyltin oxide as a catalyst can give a considerably higher yield of the desired product as compared with the use of di-n-butyltin oxide as a catalyst irrespective of the amount of moisture in the system.

Also, when di-n-butyltin oxide is used, the yield of the desired product decreases remarkably with an increase in the amount of moisture contained in the system. On the other hand, when di-n-octyltin oxide is used, a decrease in the yield is small and a high yield can be maintained even if the amount of moisture contained in the system is large.

COMPARATIVE EXAMPLE

Into a flask equipped with a stirrer, a thermometer and a distilling column are charged 750.8 g of methyl methacrylate, 268.7 g of dimethylaminoethanol containing 0.5% by weight of moisture, and 6.0 g of phenothiazine as a polymerization inhibitor. The mixture is heated with stirring until it boils. The reaction mixture is refluxed until the temperature at the top of the column reaches 95° C., and the azeotropic mixture of methyl methacrylate and water is then distilled at a reflux ratio of 10:1. When the amount of the collected filtrate (methyl methacrylate, water and a small amount of methanol) reaches 55 g, the distillation is stopped. The reaction mixture is then cooled to 80° C. and 7.5 g of di-n-butyltin oxide is added. The resulting mixture is heated until it boils. The azeotropic mixture of the methanol formed and methyl methacrylate is refluxed for 20 minutes, and the reaction mixture is then reacted while part of the azeotropic mixture is withdrawn from the system at a reflux ratio of 15:1. During the reaction, the temperature at the top of the distilling column is kept at 65°-70° C. The esterification reaction is completed in 4.5 hours. The reaction mixture is distilled under reduced pressure as it is to obtain 430.1 g of dimethylaminoethyl methacrylate. This yield corresponds to 91.2% based on the starting dimethylaminoethanol.

As is seen from comparison of this result with the results of Table 1, when di-n-butyltin oxide is used as a catalyst, the yield of the desired product is lower as compared with the case where di-n-octyltin oxide is used in a system containing a small amount of moisture, even if the moisture contained in the system is removed enough before the addition of the catalyst.

What is claimed is:

1. A process for preparing dimethylaminoethyl methacrylate which comprises subjecting methyl methacrylate and dimethlaminoethanol to transesterification, characterized by using di-n-octyltin oxide as a catalyst, there being present about 0.1 to about 0.5% by weight of moisture based on the dimethylaminoethanol.

2. A process according to claim 1, wherein the amount of di-n-octyltin oxide used is 0.1-5 mole % based on the starting dimethylaminoethanol.

3. A process according to claim 2, wherein the amount of di-n-octyltin oxide used is 0.25-2.5 mole % based on the starting dimethylaminoethanol.

4. A process according to claim 1, wherein a polymerization inhibitor is further added to the reaction system.

5. A process according to claim 4, wherein said polymerization inhibitor is selected from the group consisting of phenothiazine, hydroquinone monomethyl ether, phenyl-$\beta$-naphthylamine, para-phenylenediamine and diphenylamine.

6. A process according to claim 5, wherein said polymerization inhibitor is phenothiazine.

7. A process according to claim 1 for preparing dimethylaminoethyl methacrylate which comprises subjecting 1.2-3.5 moles of methyl methacrylate and 1 mole of dimethylaminoethanol to transesterification in the presence of 0.1-5 mole % of di-n-octyltin oxide as a catalyst based on the starting dimethylaminoethanol and optionally a polymerization inhibitor and optionally a solvent at 40°-140° C. under atmospheric pressure or a slightly reduced pressure.

* * * * *